United States Patent [19]

Clyde

[11] 4,407,954
[45] * Oct. 4, 1983

[54] FIBER FERMENTER

[76] Inventor: Robert A. Clyde, P.O. Box 983, Asheville, N.C. 28802

[ * ] Notice: The portion of the term of this patent subsequent to Sep. 28, 1999 has been disclaimed.

[21] Appl. No.: 328,125

[22] Filed: Dec. 7, 1981

Related U.S. Application Data

[63] Continuation-in-part of Ser. No. 216,310, Dec. 15, 1980, Pat. No. 4,351,905.

[51] Int. Cl.³ .......................... C12P 7/06; C12P 7/02; C12M 1/40; C12M 1/02
[52] U.S. Cl. .................................. 435/161; 435/155; 435/243; 435/253; 435/254; 435/255; 435/288; 435/316; 435/813
[58] Field of Search ............... 435/243, 253, 254, 255, 435/288, 311, 312, 313, 314, 315, 316, 813, 161, 155

[56] References Cited

U.S. PATENT DOCUMENTS 4,351,905  9/1982  Clyde ................................. 435/316

*Primary Examiner*—Robert J. Warden
*Attorney, Agent, or Firm*—D. I. Hague

[57] ABSTRACT

A method and apparatus particularly useful for producing alcohols such as ethanol from sugars such as glucose. The apparatus comprises a container for holding a selected nutrient solution, a substrate comprising a multiplicity of fibers suitable for supporting a selected converting organism supported within the container and means for moving one of the substrate and the nutrient solution relative to the other at a speed slightly below that at which the organism becomes detached from the substrate while maintaining sufficient contact time between the nutrient solution and the converting organism to produce a satisfactory yield.

20 Claims, 6 Drawing Figures

FIBER FERMENTER

CROSS-REFERENCE TO RELATED APPLICATIONS

The present application is a continuation-in-part application to U.S. patent application Ser. No. 216,310, entitled "HORIZONTAL FERMENTER", filed on Dec. 15, 1980, in the name of Robert A. Clyde now U.S. Pat. No. 4,351,905.

FIELD OF THE INVENTION

The present invention relates to methods and apparatus for manufacturing chemicals such as ethanol and other alcohols from nutrient mediums such as sugar solutions. More particularly, the invention relates to improved methods and apparatus for manufacturing ethanol and other alcohols or acids from sugar solutions that provide a faster reaction rate.

DESCRIPTION OF THE PRIOR ART

As world reserves of petroleum are rapidly depleted, an increasing effort is being directed toward the development of alternate sources of energy. Chemists have known for almost 200 years that the cellulose in biological and agricultural residues such as sawdust and corn stover can be converted into monomeric sugars such as xylose, pentoses, hexoses, glucose and galactoses. These simple sugars can then be biologically converted by selected microorganisms into alcohols such as ethanol which is a useful alternate transportation fuel that can either be blended with gasoline (gasohol) to extend present supplies or used directly with appropriate modifications to an internal combustion engine. The problem has always been to produce fuel grade alcohols at an economically competitive price.

In U.S. patent application Ser. No. 216,310, filed on Dec. 15, 1980, and entitled "HORIZONTAL FIBER FERMENTER", I have disclosed a fermenter which is particularly useful for producing alcohols such as ethanol from sugars such as glucose. The fermenter comprises an ICR (Immobilized Cell Reactor) container for allowing the uninhibited growth of an organism suitable for converting a selected sugar solution into a selected alcohol, the container having a port for receiving the sugar solution, exhaust ports for discharging $CO_2$ and a flow of excess organisms, a port for removing the alcohol, a support subtrate comprising a multiplicity of fibers suitable for supporting the selected converting organisms, means for supporting the substrate within the container and means for physically detaching the organisms from the support substrate. Cotton, orlon, nylon and polyester were found to be satisfactory fibers. In order to provide sufficient contact between the sugar solution and the converting organism to produce a satisfactory alcohol yield, the sugar solution is, in a continuous process, pumped slowly through the container, e.g. at a rate of about one foot per hour.

SUMMARY OF THE INVENTION

I have now discovered that in a fermenter as described in the above-identified U.S. patent application Ser. No. 216,310, a faster reaction results by moving one of the sugar solution and the converting organism at high speed relative to the other while maintaining sufficient contact time between the solution and the organism to produce a satisfactory yield. In accordance with one preferred embodiment of the invention the desired high speed relative motion between the sugar solution and the converting organism is achieved by moving the organism supporting fiber substrate within the fermenter. In accordance with another preferred embodiment the desired high speed relative motion is achieved by continuously recirculating the sugar solution through the supporting fiber substrate and, after a reasonable concentration of alcohol is formed, removing such alcohol by distillation or solvent extraction, and recycling the sugar back to the reactor.

The invention and its features and advantages will become more apparent by referring to the accompanying drawings and the the ensuing description of the preferred embodiments.

DETAILED DESCRIPTION OF THE INVENTION

Because fermenters are well known, the present description will be directed in particular to elements forming part of or cooperating directly with apparatus in accordance with the present invention. It is to be understood that elements not specifically shown or described may take various forms well known to those having skill in the fermenter art.

Figure 1:
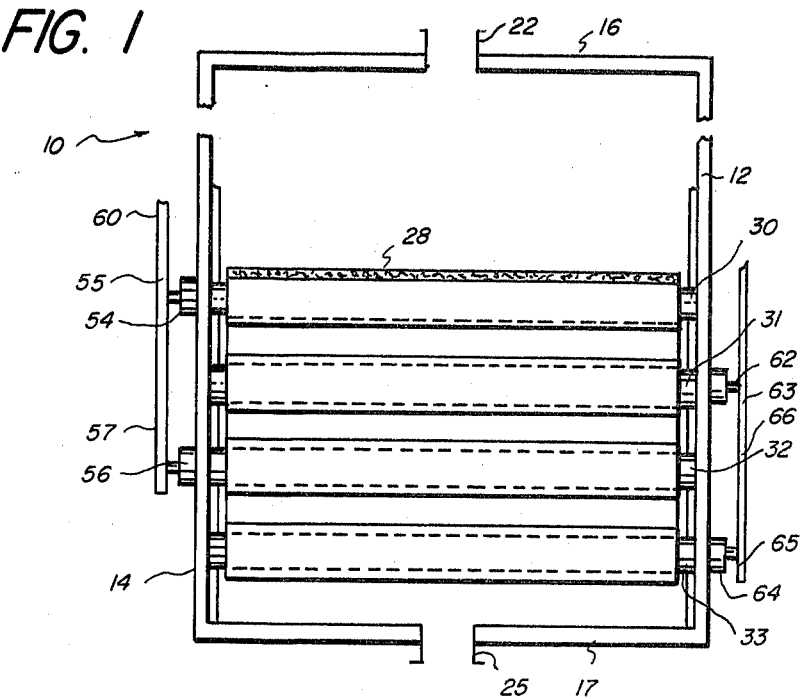
FIGS. 1, 2 and 3 are plan, end and side views, respectively, of a fermenter constructed in accordance with the present invention.
Figure 2:
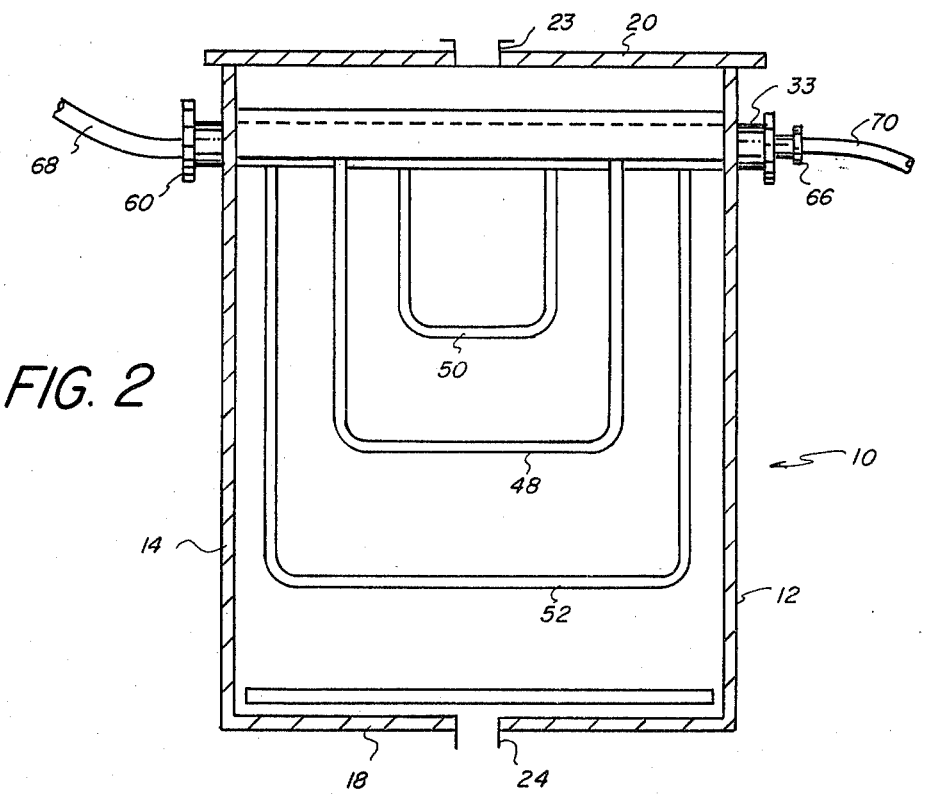
Figure 3:
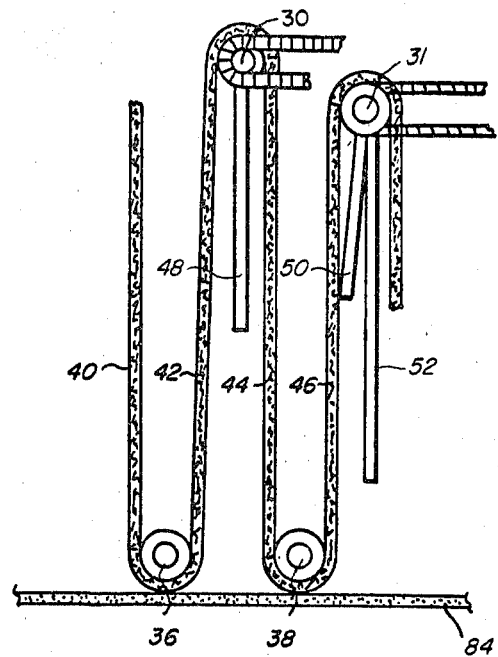

Referring now to FIGS. 1, 2 and 3 there is shown top, front and side views, respectively, of a fiber fermenter incorporating the features of this invention. It will become obvious from the discussion of this fiber fermenter, that biomass or bacteria are free to grow at an uninhibited rate while at the same time any $CO_2$ by-product is readily removed from the fermenter. As shown, there is a container 10 having side panels 12 and 14, a front panel 16, a rear panel 17 and bottom panel 18. There is also shown a removable top or access panel 20. As will be discussed hereinafter, there is also included a nutrient entry port 22, $CO_2$ port 23, an excess biomass exit port 24 and an alcohol output port 25. According to the embodiment shown in FIGS. 1, 2 and 3 of this invention, container 10 includes a porous fiber webbing 28 supported at an upper position by rollers 30, 31, 32 and 33 which rollers are supported by side panels 12 and 14. Also shown are lower spacer bars 36 and 38 which hang between and are supported by webbing layers 40, 42, 44 and 46. Spacer bars 36 and 38 can be of any suitable diameter, but ¼" rods have been found effective. As can be more clearly seen in the side view of FIG. 4, alternate top roller supports such as roller bars 30 and 32 include striker bars 48 of a first length while roller bars 31 and 33 include striker bars 50 and 52 of second and third lengths, respectively. As shown in FIG. 1 pivot shafts 54 and 56 of the roller bars 30 and 32, respectively, extend through the side panel 14. Each of these pivot shafts has attached thereto a spur gear such as is shown at 55 and 57. A connecting chain 60 is connected around and meshes with the spur gears 55 and 57. Likewise, pivot shafts 62 and 64 of the roller bars 31 and 33, respectively, extend through the side panel 12. Each of these pivot shafts has attached thereto a spur gear such as is shown at 63 and 65. A connecting chain 66 is connected around and meshes with the spur gears 63 and 65. If desired, the striker bars and roller bars may be hollow and the fermenter provided with input tubing 68 and output tubing 70. Such an arrangement allows water to be circulated through the striker bars to help maintain the nutrient solution at a desired temperature.

Figure 4:
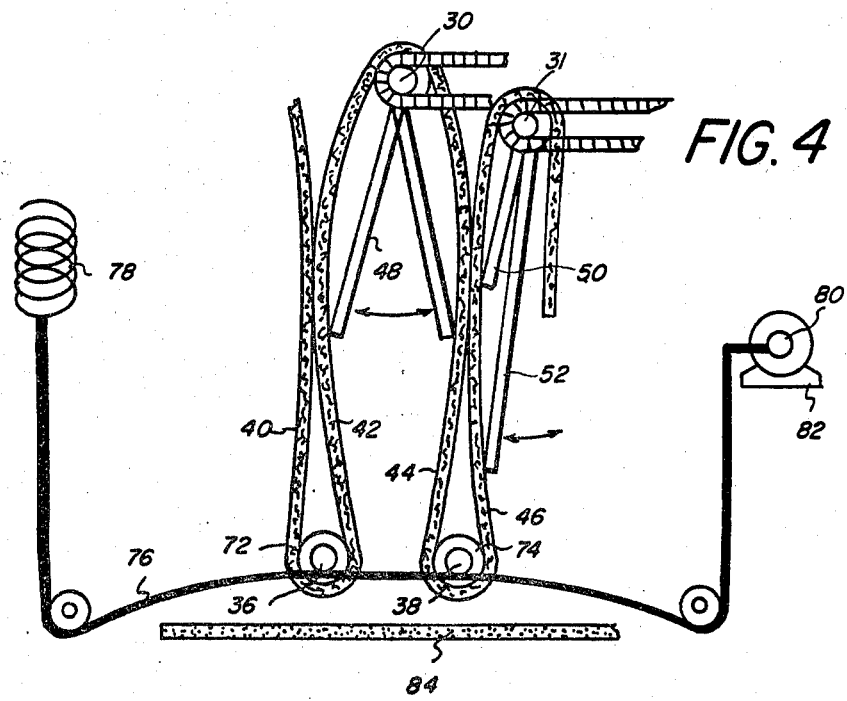
FIG. 4 shows the detailed operation of the striker bars of the fermenter of FIGS. 1, 2 and 3 for removing excess biomass.

As shown in FIG. 4, the lower spacer bars 36 and 38, have pulleys 72 and 74, respectively, to which a wire 76 is attached. One end of the wire 76 is connected to a spring 78 and the opposite end to an eccentric shaft 80 of a motor 82. During the normal running of the fermenter, the fiber webbing 28 is moved back and forth through the nutrient solution by the shaft 80 and motor 82 while the striker bars 48, 50 and 52 are moved (by means not shown) in the same direction as the wire 76 so that no flexing of the fibers occurs. When excess organisms have built up on the webbing, the striker bar 48 is then moved in one direction and the striker bars 50 and 52 in the opposite direction so that they interlock with the striker bar 48 and cause a plurality of flexes in the fiber webbing 28. The flexing of the webbing 28 knocks loose the excess organisms which fall into a conveyor belt 84. When excess organisms are on the belt 84, the striker bars 48, 50 and 52 are left at an angle, as shown in FIG. 4, leaving space between the webbing 28 and belt 84 so that the belt 84 can be moved to remove the excess organisms. When the removal procedure is completed the striker bars 48, 50 and 52 are moved to the position shown in FIG. 3 which permits the webbing 28 to contact the belt 84. The porous fiber webbing 28 may be made of any suitable material such as cotton, polyester, orlon, nylon, rayon, acetate, wool, polypropylene or any combination of such materials. Although the above mentioned materials are preferred in the conversion of sugar to alchol, in certain fermenters which directly convert organic material such as corn stalks to alcohol by means of a simultaneous biological process or by the use of a bacteria such as Clostridium, species organic webbing or fibers will not be satisfactory since the bacteria would also operate on such fibers. In such situations, fibers or webbing of ceramic or fiberglass is preferred. The DuPont Company has organic aramid fibers called Nomex and Kevlar. Several companies have ceramic fibers. Carborundum has Fiberfrax, 3 M has Nextel, Celanese has Celiox, Newtex Industries has Zetex, Amatex has Zetex, and Armco has Refrasil. Webbing can preferably be about one quarter inch or less apart and made of strings about one-eighth inch in diameter or less. A Du Pont plastic webbing Vestar has been found to be particularly effective and cheesecloth is a good cotton webbing. Also, projections (not shown) may be attached to the top support bars to prevent the webbing from slipping.

In operation, it is first necessary in running a fermenter to prepare a culture such as a sugar nutrient solution by sterilizing, inoculating and incubating the nutrients. The sugar nutrient may include such sugars as pentoses, hexoses, xyloses, glucose, sucrose and perhaps galactose. This nutrient solution depending upon the type of bacteria to be grown, may for example consist of glucose, yeast extract $KH_2PO_4$, $(NH_4)_2SO_4$, and $MgSO_4$ as clearly described and understood by those skilled in the art. The sugar solution may, of course, be obtained by the hydrolysis of a suitable organic material such as corn stalks. The selected bacteria such as Zymononas mobilis which ferments glucose, Kluyveromyces fragilis which ferments lactose or Clostridium thermosaccharolyticium which ferments five carbon sugars is then transferred in any suitable manner well known by those skilled in the art and is incubated at a suitable temperature and placed in the sugar solution. In the case of Z. mobilis a suitable temperature is between 30 and 35 degrees centigrade. The culture then will start a rapid uninhibited growth attached to the fiber webbing and convert the sugar to ethanol. A yeast, Pachysolen tannophilus ferments glucose as well as xylose (a five carbon sugar). Clostridium can also produce Butanol and acetone.

To speed the reaction time, the webbing 28 is moved relative to the sugar solution, or, as described hereinbelow with reference to FIG. 6, the sugar solution is moved relative to the webbing. The rate of relative movement between the sugar solution and the webbing should be sufficient for thorough mixing without causing the converting organism to become detached from the webbing. Tests have shown that organism detachment occurs at a certain definite rate of movement. A test suitable for use in the present invention to evaluate the adhesion between a selected organism and a selected fiber webbing consists of pumping the organism cells up through an orifice and then radially across a plate to which the fiber webbing is attached. At a particular pumping rate the sheer forces are too great and the organism becomes detached from the webbing. The optimum rate of relative motion between the sugar solution and the webbing 28 must then be slightly less than the above-noted rate. A device for measuring organism adhesion is commercially available from Dr. Fowler of the Chemical Engineering Dept. at the University College of Swanesa in England or from an associated company. Because of the uninhibited growth of the biomass, after approximately ten (10) days to two (2) weeks, the fermenter may become clogged such that free flow of the sugar solution and the $CO_2$ and the removal of alcohol is no longer possible. In that event, excess bimass can be readily removed, as illustrated in FIG. 4 by moving the drive chain 60 in a clockwise direction and moving the drive chain 66 in a counterclockwise direction. As the drive chain 60 moves, the striker bars 48 are rotated so that they strike layers 42 and 44 of webbing 28 which in turn are moved so that these layers strike layers 40 and 46 of the webbing. As the drive chain 66 moves, the striker bar 50 strikes the upper portion of layers 40 and 46 and the striker bar 52 strikes the lower portion of layers 40 and 46 so that these layers strike layers 42 and 44 with a bowed action. The biomass knocked loose by the action of the striker bars 48, 50 and 52 is then discharged by the conveyor belt 84 through exhaust post 24. It will be appreciated, of course, that the spacer bars 36 and 38 are not attached to the fermenter and therefore are free to move, as shown in FIGS. 3 and 4, back and forth or up and down during the movement of the drive chains 60 and 66 as determined by the webbing 28.

Figure 5:
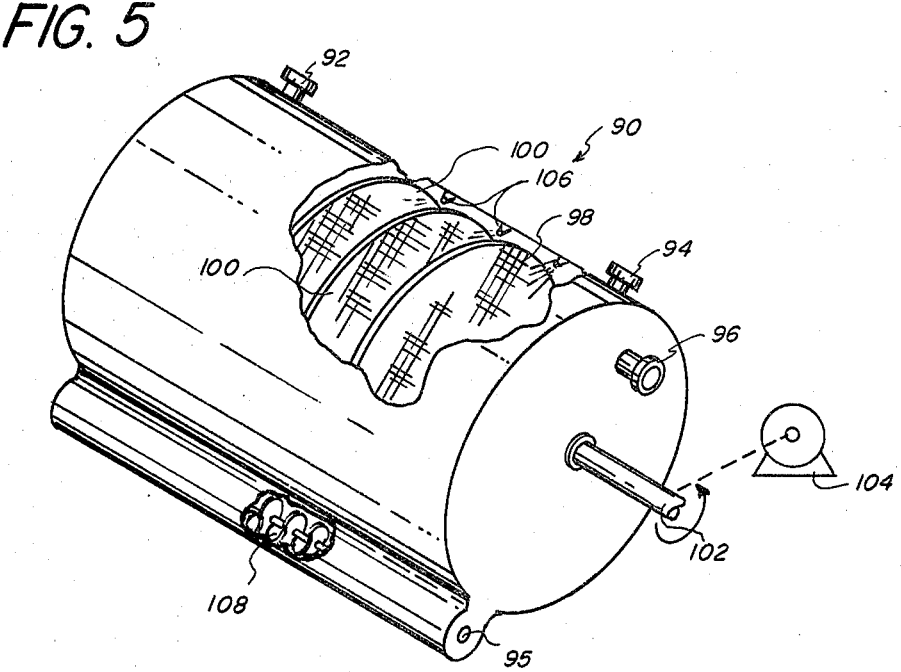
FIG. 5 shows an alternative embodiment of the fermenter.

An alternative embodiment of a fermenter in which the fiber webbing is moved relative to the sugar solution is shown in FIG. 5. The fermenter 90 includes a nutrient input port 92, $CO_2$ and biomass exhaust ports 94 and 95, and an alcohol output port 96. Fiber webbing 98 is mounted on a plurality of supportive filters 100 which are rotatably mounted on a shaft 102. In operation the fermenter 90 is ¾ filled with nutrient solution and a selected bacteria is added. The filters 100 and the fiber webbing 98 supported thereon are then rotated by a motor 104. When the uninhibited growth of biomass clogs the fermenter 90, nozzles 106 are turned on to wash off the filters 100. A screw conveyor 108 is also turned on to remove through port 95 the biomass that is washed down to the bottom of the fermenter 90.

Figure 6:
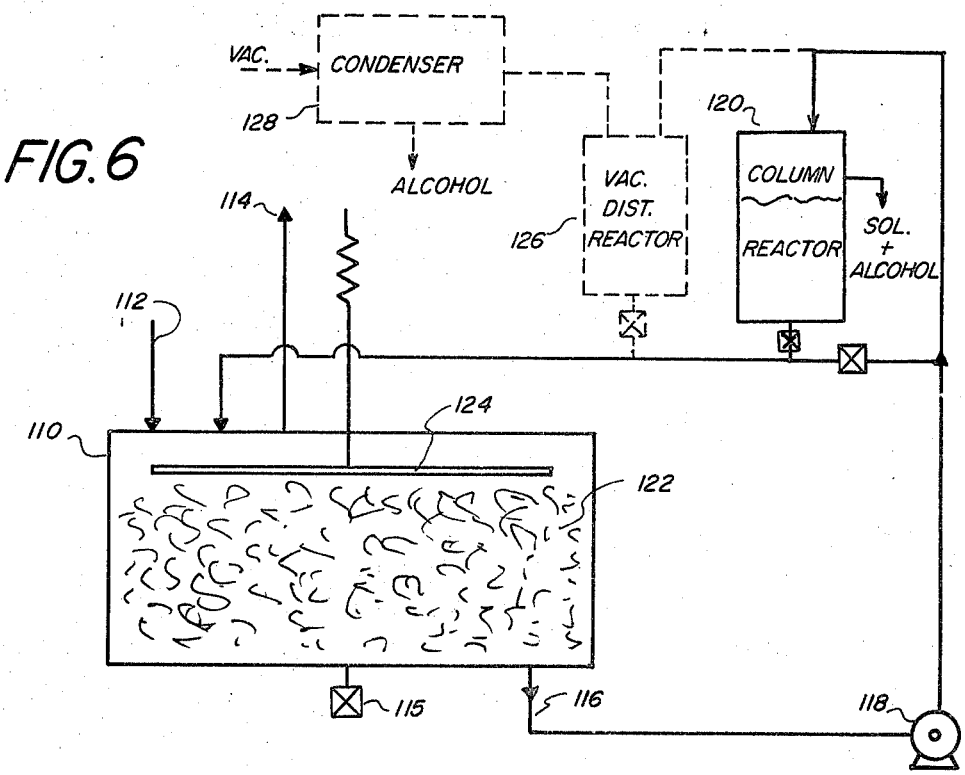
FIG. 6 shows still another alternative embodiment of the fermenter.

Instead of moving the fiber webbing, the nutrient solution can be moved at high speed relative to the webbing, as shown in FIG. 6. In this embodiment the fermenter 110 includes a nutrient input port 112, $CO_2$ and biomass exhaust ports 114 and 115 and an output port 116. A pump 118 is connected to the output port 116 and to a column 120 or vacuum reactor 126. In operation the fermenter 110 is first filled with flexible fiber webbing 122 and then filled with a selected nutrient solution and a selected converting organism. At the beginning of the process the nutrient solution is continuously circulated through the webbing 122 by the pump 118 for an hour or so at a rate of approximately 5 feet per hour or greater until a reasonable concentration of alcohol is formed. When the increasing alcohol concentration starts to inhibit the reaction, the pump 118 then pumps the liquid in the fermenter to the column reactor 120 where the alcohol is removed by solvent extraction. Alternatively, the alcohol can be removed by distillation as shown in dotted lines. In this method, the liquid in the fermenter is pumped to a vacuum distillation reactor 126 where the liquid is heated to drive off the alcohol. The alcohol is then condensed in a condensor 128. If the distillation method is used, vacuum is employed to keep the temperature down. If the solvent extraction method is used, dodecanol is preferably used as the solvent. Whichever of the two methods of alcohol removal is used, the sugar solution is returned to the fermenter for re-circulation through the webbing 122. In laboratory runs it was observed that most the $CO_2$ bubbles occur in first few inches. To remove excess biomass from the webbing, plungers 124 located at the top of the fermenter are activated to press and flex the fibers. Holofil ®, a polyester from DuPont, is a good fiber for this application because it is elastic and will spring back to its original shape after being compressed.

An advantage of this embodiment is that a smaller fermenter can be used. A significant cost factor in a fermentation system is the cost of transporting the raw material (corn stalks, wood, etc.) to the fermenter. Since a smaller fermenter is used in this embodiment and the fibers are light in weight the fermenter could be mounted on a truck and moved to the source of the raw material or it could be used on a ship transporting a sugar solution.

The following examples will serve to further illustrate the present invention.

REFERENCE EXAMPLE

A cotton string about ⅛ inch in diameter was taken off a Fulflo Filter (made by the Carborundum Co.) and put with random orientation into a horizontal glass fermenter 27″ long and 1¾″ diameter and sterilized. A culture of Zymomonas mobilis was obtained from the American Type Culture Collection, put into sterile solution of 10% sugar (dextrose), 1% yeast extract, 0.1% $KH_2PO_4$, 0.1% $(NH_4)_2SO_4$ and 0.05% $MgSO_4.7H_2O$ and incubated at 30° C. overnight, then put into the fermenter with more of the above nutrient media and allowed to stand at 31° C. overnight. No $CO_2$ was observed coming off (no bubbles). Nutrient media was pumped thru the fermenter for 3 days; after the third day some evolution of $CO_2$ was observed.

EXAMPLE 1

The same procedure as above was followed, except after the solution was put into the fermenter, the entire fermenter was rocked back and forth, one cycle per second through a distance of 2 centimeters. After one day rather vigorous evolution of $CO_2$ was observed, considerably more than that in reference example in 3 days. Visual examination of the string showed presence of more bacteria than in the reference example.

EXAMPLE 2

The same procedure was followed in the reference Example except the string was rotated inside the fermenter at about 30 rpm. As in example 1, after one day of rotation, a vigorous evolution of $CO_2$ was observed, and bacteria were present on the string.

The invention has been described in detail with particular reference to illustrative preferred embodiments thereof, but it will be understood that variations and modifications can be effected within the spirit and scope of the invention. For example, in addition to alcohol, it is possible by selection of the proper bacteria and nutrient solution to obtain other chemicals. For example, the use of bacteria Propionibacterium acidi propionici can generate Propionic and acetic acid at less than one fourth of the present manufacturing costs. In addition, Pseudomonas species may be attached and can convert 2-4D to $CO_2$ and water. This process is clearly described in a article by Pierce and Kidd in the July 23rd, 1980 Chemical Week magazine, page 39. Fungi such as *Rhizopus arrhizus* and *R. oligosporus* can be used to take up and concentrate uranium. The fungus Monilia sp. will convert cellulose to alcohol. Cladosporium is a valuable fungus for reactions, also Thiobacillus.

Although it has been found that the string fermenter as discussed above provides large areas for the attachment of the bacteria, it is possible to create a higher contact area on the string or ceramic fiber by the use of a high area alumina applied to the string or ceramic fiber. Use of such high area alumina is described in a paper entitled, "Dispal M, a Unique, New and Versatile Alumina for the Ceramic Industry" by Robert Butler of Continental Oil Company in SAE paper 730276 presented at the American Ceramics Society, Nov. 2, 1971. Mr. Butler recommends heating to 900° F., but I have found that a lower temperature results in a more positive charge which attracts negative bacteria better.

A white powder of colloidal alumina identified as Baymal and provided by Du Pont is suitable for such coating. Each particle of the powder consists of a porous aggregated mass of submicroscopic fibrous crystals or "fibrils" of boehmite alumina (A100H). A coating of this alumina is especially effective when supplied with a positive charge such that particles of negatively charged materials are attracted. A coating of terra sigillata can also be applied to ceramic fibers to increase the surface area.

Fiberglass fibers can also be used. Fiberglass also has a smooth surface which is difficult for the organisms to stick to. To increase the surface area, the fiberglass can be etched with caustic.

I claim:

1. In a method for allowing the growth of an organism suitable for converting a selected nutrient medium into a selected chemical including the steps of:
   (a) sterilizing, innoculating and incubating the nutrient medium;
   (b) incubating the converting organism;
   (c) placing the nutrient medium and the converting organism in a container having a substrate supported therein comprising a multiplicity of fibers suitable for supporting the organism, the improvement comprising:
   (d) moving one of the converting organism and the nutrient medium relative to the other at a speed which is slightly below the speed at which the converting organism becomes detached from the supporting substrate while maintaining contact between the converting organism and the nutrient medium for a time period sufficient to produce a satisfactory chemical yield.

2. The method according to claim 1 wherein the moving and maintaining step comprises rotating the fiber substrate within the container.

3. The method according to claim 1 wherein the moving and maintaining step comprises moving the fiber substrate back and forth through the nutrient medium.

4. The method according to claim 1 wherein the moving and maintaining step comprises continuously recirculating the nutrient medium through the fiber substrate.

5. The method according to claim 1 wherein the nutrient medium is a sugar solution and the selected chemical is an alcohol.

6. The method according to claim 5 wherein the sugar solution is selected from the group consisting of glucose, sucrose, pentose, xylose and galactose.

7. The method according to claim 5 wherein the converting organism is selected from a group consisting of species in the genera of Zymononas, Clostridium, Pachysolen and Kluyveromyces.

8. The method according to claim 5 wherein the selected alcohol is ethanol.

9. The method according to claim 5 wherein, when the sugar solution is reacted for a length of time until the alcohol produced starts to inhibit the reaction, the sugar-alcohol solution is removed from the container, some alcohol is removed and the sugar solution is returned to the container.

10. Apparatus for allowing the growth of an organism suitable for converting a selected nutrient medium into a selected chemical comprising:

a container suitable for containing the nurient medium, the container including a port for receiving the nutrient medium, an exhaust port for discharging a flow of excess organisms and a port for removing the selected chemical;

a porous support substrate mounted within the container, the substrate comprising a multiplicity of fibers suitable for supporting the selected organism; and means for moving one of the support substrate and the nutrient medium relative to the other at a speed slightly below the speed at which the converting organism becomes detached from the support substrate and for maintaining contact between the support substrate and the nutrient medium for a period of time sufficient to produce a satisfactory chemical yield.

11. The apparatus according to claim 10 further comprising means for physically detaching the converting organism from the support substrate.

12. The apparatus according to claim 10 wherein the multiplicity of fibers are in the form of a porous webbing.

13. The apparatus according to claim 10 wherein the multiplicity of fibers are in the form of cotton string.

14. The apparatus according to claim 10 wherein the multiplicity of fibers are in the form of a ceramic material.

15. The apparatus according to claim 10 wherein the multiplicity of fibers are in the form of a polyester.

16. The apparatus according to claim 10 wherein the moving and maintaining means comprises a pump for recirculating the nutrient medium through the support substrate.

17. The apparatus according to claim 10 wherein the moving and maintaining means comprises means for moving the support substrate back and forth through the nutrient medium.

18. The apparatus according to claim 10 wherein the moving and maintaining means comprises means for rotating the support substrate through the nutrient medium.

19. The apparatus according to claim 10 further comprising means for removing partially reacted nutrient medium from the container, extracting the chemical therefrom and then returning the nutrient medium to the container.

20. The apparatus according to claim 10 wherein the container and the moving and maintaining means are mounted on a portable conveyance.

* * * * *